(12) United States Patent
Riedinger et al.

(10) Patent No.: US 9,821,060 B2
(45) Date of Patent: Nov. 21, 2017

(54) HEAT-SENSITIVE NANOPARTICLE SYSTEM

(71) Applicant: FONDAZIONE ISTITUTO ITALIANO DI TECNOLOGIA, Genoa (IT)

(72) Inventors: Andreas Riedinger, Genoa (IT); Teresa Pellegrino, Genoa (IT); Pablo Guardia Giros, Barcelona (ES); Alberto Curcio, Torre Annunziata (IT); Roberto Cingolani, Ceranesi (IT); Liberato Manna, Genoa (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 183 days.

(21) Appl. No.: 14/763,180

(22) PCT Filed: Jan. 28, 2014

(86) PCT No.: PCT/IB2014/058615
§ 371 (c)(1),
(2) Date: Jul. 24, 2015

(87) PCT Pub. No.: WO2014/115126
PCT Pub. Date: Jul. 31, 2014

(65) Prior Publication Data
US 2015/0359887 A1   Dec. 17, 2015

(30) Foreign Application Priority Data
Jan. 28, 2013   (IT) .............................. TO2013A0065

(51) Int. Cl.
*A61K 41/00* (2006.01)
*A61K 47/48* (2006.01)
(Continued)

(52) U.S. Cl.
CPC ........ *A61K 41/0052* (2013.01); *A61K 31/704* (2013.01); *A61K 47/48215* (2013.01);
(Continued)

(58) Field of Classification Search
CPC ................. A61K 9/0009; B82Y 25/00; G01N 33/54326; H01F 1/0054
See application file for complete search history.

(56) References Cited

U.S. PATENT DOCUMENTS

2010/0040549 A1* 2/2010 Halas ................. A61K 41/0028
424/9.1

OTHER PUBLICATIONS

Huang et al., Gold nanoparticles: Optical properties and implementations in cancer diagnosis and photothermal therapy. J. of Adv. Research, vol. 1, Issue 1, Jan. 2010, pp. 13-28.*
(Continued)

*Primary Examiner* — Alexandre Ferre
(74) *Attorney, Agent, or Firm* — Marshall, Gerstein & Borun LLP

(57) ABSTRACT

A heat-sensitive system comprising at least one nanoparticle bound covalently to at least one thermolabile molecule comprising an azo —N═N— functional group —N═N— in turn bound covalently to at least one active molecule selected from a fluorophore molecule and a drug is disclosed. The system converts an electromagnetic radiation into thermal energy exposed to an alternating magnetic field. Uses of the system are also disclosed.

13 Claims, 8 Drawing Sheets

(51) Int. Cl.
*A61K 31/704* (2006.01)
*A61K 49/00* (2006.01)

(52) U.S. Cl.
CPC .... *A61K 47/48884* (2013.01); *A61K 49/0043* (2013.01); *Y10T 428/2982* (2015.01)

(56) References Cited

OTHER PUBLICATIONS

Ahonen et al., Optical switching of coupled plasmons of Ag-nanoparticles by photoisomerization of an azobenzene ring, Phys. Chem. Chem. Phys., 9:651-8 (2006).
Lee et al., Nanoparticle assemblies with molecular springs: A nanoscale thermometer, Angew. Chemie, 117:7605-8 (2005).
Lin et al., Design of an amphiphilic polymer for nanoparticles coating and functionalization, Small, 4(3):334-41 (2008).
Luo et al., Light-tunable thermosensitivity of polymer-coated gold nanoparticles achieved by light-controlled molecular recognition, Macromolecular Chem. Phys., 212:1360-5 (2011).
Riedinger et al., Subnanometer local temperature probing and remotely controlled drug release based on azo-functionalized iron oxide nanoparticles, Nano Lett., 13:2399-406 (2013).
Subedi et al., Preparation and characterization of solid lipid nanoparticles loaded with doxorubicin, Eur. J. Pharm. Sci., 37(3-4):508-13 (2009).
International Search Report and Written Opinion, International Application No. PCT/IB2014/058615, dated May 8, 2014.

\* cited by examiner

HEAT-SENSITIVE NANOPARTICLE SYSTEM

CROSS-REFERENCE TO RELATED APPLICATIONS

This is the U.S. national phase of PCT/IB2014/058615, filed Jan. 28, 2014, which claims the benefit of Italian Patent Application No. TO2013A000065, filed Jan. 28, 2013.

TECHNICAL FIELD

The present invention relates to a system comprising a paramagnetic nanoparticle and a temperature-sensitive molecular probe. Said system can be used for measuring the temperature of said paramagnetic nanoparticles when irradiated with alternating magnetic fields or for carrying drugs associated with the nanoparticles with heat-controlled release.

BACKGROUND ART

It is known that magnetic particles (MNPs) are used as heat mediators for the treatment of tumour tissues in magnetically induced hyperthermia treatment[1,2,3,4,5,6,7].

Reaching of the treatment temperature (41-45° C.) in the target site is linked to the presence of a high concentration (in the order of grams/liter) of magnetic material in a confined volume[8,9]. This characteristic obviously cannot be obtained when the tumours are located in parts of the organism that are difficult to reach[10].

The use of magnetic nanoparticles has also been proposed for carrying drugs which are released due to the heat generated by exposure of the nanoparticle to an alternating magnetic field[11,12,13] (AMF).

Recently, it has been shown that even if irradiation with AMF of the nanoparticles in the vicinity of the tumour cells does not produce heat at macroscopic level, the magnetic nanoparticles are able to induce apoptosis of the tumour cells when exposed to an alternating magnetic field[3,14]. This effect has been associated with the hypothesis that significant heating occurs only locally, i.e. in the vicinity of the surface of the magnetic nanoparticle[15]. Furthermore, advantageously, the absence of an increase in the macroscopic temperature reduces the side effects connected with heating of the healthy tissues[27,29].

Friedman and collaborators have monitored the local temperature increase in magnetic nanoparticles bound to the surface of some cells, observing the activation of temperature-sensitive TRPV1 ionic channels. These protein, channels allow the inflow of calcium ions from the outside to the inside of the cell if the local temperature reaches values of 40° C.[27]. Also in this case, although an increase in the flow of calcium ions has been recorded due to activation of the nanoparticles under AMF, no variation has been recorded in the macroscopic temperature.[14]

Today, therefore, a reliable system is needed for measuring the local temperature profile of magnetic nanoparticles excited by means of an alternating magnetic field.

The traditional methods for thermal characterisation (for example measurements of the specific absorption rate or SAR) are not suitable for the measurement of localised effects. The first-reason is that said measurements require the performance of experiments with highly concentrated dispersions of nanoparticles in which macroscopic heating of the environment occurs and in which interactions between the particles cannot be ruled out.

Furthermore the definition of SAR is valid only for experiments conducted in conditions near to adiabatic conditions, which are a long way from the isothermal system conditions that occur for a diluted solution in which the heat losses are dominant.

Lastly, the temperature recorded corresponds to the macroscopic temperature of the medium in which the nanoparticles are dispersed rather than to their surface temperature.

Recently temperature mapping strategies have been developed to measure the surface temperature of the nanoparticles[16,17].

Jacobsen et al. have reported a method for measuring the molecular temperature based on the dehybridization of double helixes of DNA bound to gold nanoparticles which occurs upon application of an electromagnetic field modulated at radio frequencies[18].

This effect has been attributed to local heating of the gold nanoparticles induced by the parasitic currents[19].

Kotov et al.[30] have developed a molecular thermometer based on an elastic molecular nanosystem assembled on gold nanoparticles and able to measure the local temperature variations. In their system, gold nanoparticles are bound to nanoparticles of CdTe by means of a polymeric spacer which acts as a molecular elastic element (or molecular spring). Since a temperature variation in the range from 20 to 50° C. causes an expansion of the polymer, the exciton-plasmon interaction of the pair of nanocrystals varies, with consequent variation in the fluorescence signal. This system, while guaranteeing a high spatial resolution, has some limitations due to the operating principle: i) the system can be applied only to gold nanoparticles; ii) the variation in the distance between the plasmonic nanoparticle and the semiconductor nanoparticle must fall within a precise range, such as to guarantee the increase in fluorescence. Temperature measurements at the nanoscale have been recently reported also by Carlos et al[20]. This group has developed a luminescent molecular thermometer based on magnetic nanoparticles coated by silica supports impregnated with rare earth complexes. The temperature dependence of the $Tb^{+3}$ ion emission line in relation to the $Eu^{3+}$ ion emission line, which instead remains constant, allows measurement of the absolute temperature in solution with an accuracy of 0.5° C. and in a very wide temperature range, also comprising the physiological range (around 37° C.)[20]. Furthermore, said system, since it contains magnetic nanoparticles, has been proposed for measuring the temperature in situ and in real time of the surface of magnetic nanoparticles when exposed to hyperthermia treatment, but so far the system has never been applied for said purpose.

In order to measure the temperature at the surface of magnetic nanoparticles, Rinaldi et al.[29] have developed a system based on iron oxide coated by a fluorescent polyacrylamide polymer, in which the variation in the fluorescence intensity of the benzofuran-based fluorophore bound to the polymer is correlated with the temperature variation at the surface of the iron oxide exposed to AMF. Following the application of an AMF with appropriate magnetic field frequency and amplitude, the variation in fluorescence intensity of the fluorophore indicates a local temperature at the surface of the nanoparticles higher than 35° C., corresponding to the phase transition temperature of the polymer at the surface of the magnetic nanoparticles. This fluorescence variation occurs also if the macroscopic temperature of the system remains stable at 20° C. When the AMF field is switched off, the temperature of the nanoparticles returns to that of the solution in which they are immersed. In this system, only temperature variations around the transition value, specifically 35° C., can be monitored; it is not possible to measure any temperature profile at the surface of the nanoparticles.

Moreover, all the methods used so far for measuring temperature at the nanoscale are specific for certain types of nanoparticles (for example gold) and therefore cannot be extended to magnetic nanoparticles, or nanoparticles lacking in spatial information. Therefore, the use of said methods does not allow the collection of data useful for mapping the temperature gradients around the nanoparticles exposed to an alternating magnetic field. This information is fundamental for predicting the thermal effects of magnetic nanoparticles subjected to AMF and for designing new therapeutic agents based on magnetic nanoparticles with heat-mediated drug release.

DISCLOSURE OF INVENTION

The object of the present invention is therefore to provide a new system for measuring the surface temperature of magnetic nanoparticles following stimulation by means of an alternating magnetic field which is also able to detect the mapping of the temperature gradients around these nanoparticles.

Said object is achieved by the present invention, relative to a system and its uses according to claims.

BRIEF DESCRIPTION OF THE DRAWINGS

The present invention will now be described in detail with reference to the figures of the accompanying drawings, in which.

BEST MODE FOR CARRYING OUT THE INVENTION

Figure 1:
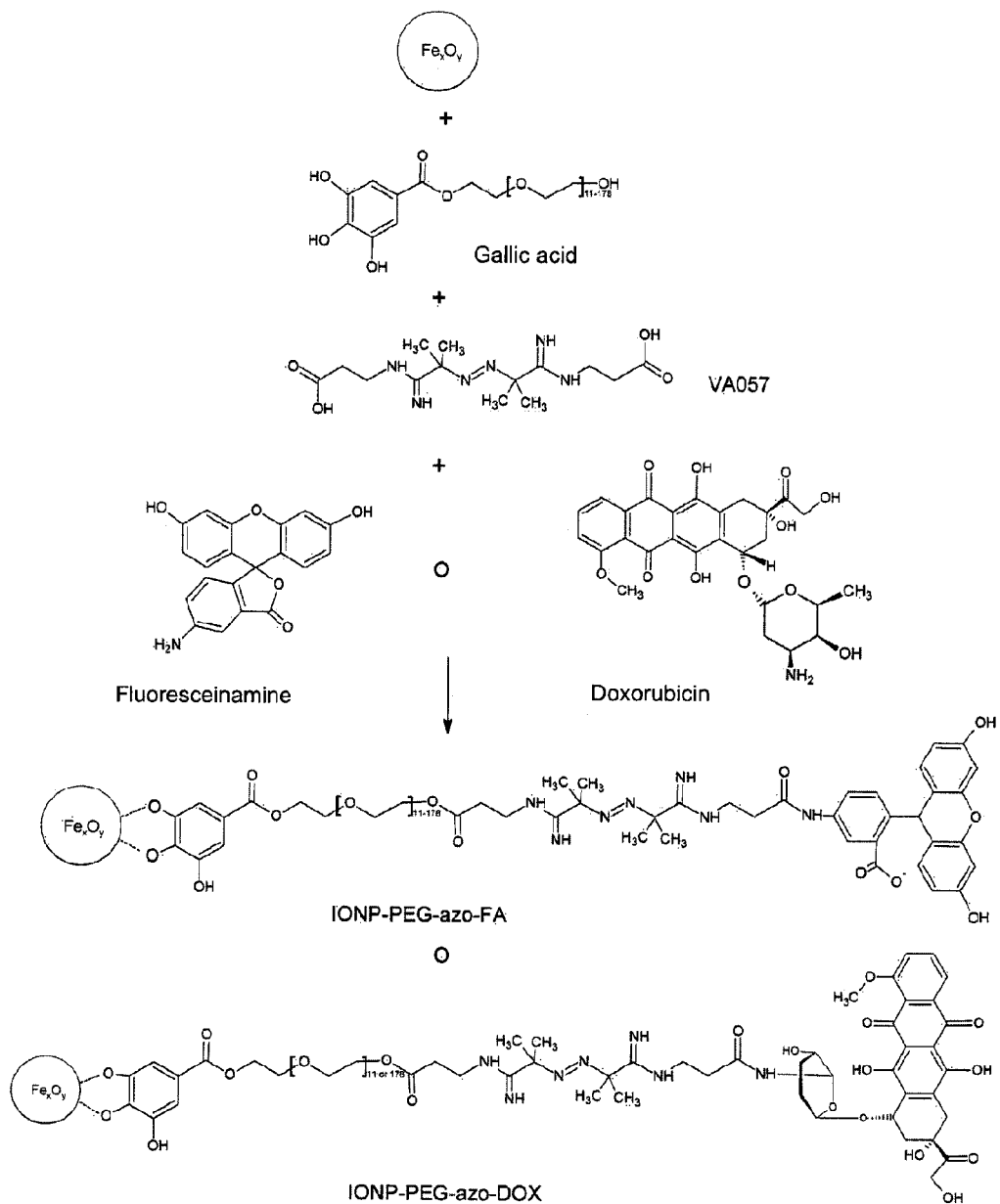
FIG. 1 illustrates a summary diagram for preparation of the system according to the invention.

According to a first aspect of the invention, a heat-sensitive system is provided comprising at least one nanoparticle able to convert an electromagnetic radiation into thermal energy when it is exposed to an alternating magnetic field. In the present text "nanoparticle" means a particle formed of molecular aggregates with a diameter between 10 and 25 nm.

The nanoparticle is made of a material which has a superparamagnetic behaviour at ambient temperature, preferably selected from the group consisting of iron oxide and ferrites.

In the system of the invention, one or more thermolabile molecules comprising an azo (—N=N—) functional group are bound covalently on the surface of the nanoparticle. In particular, thermolabile molecules selected from the group consisting of (2,2'-Azobis[N-(2-carboxyethyl)-2-methylpropionamide]hydrate), (2,2'-Azobis[2-methyl-N-(2-hydroxyethyl)propionamide), 2,2'-Azobis(2-methylpropionamidine) dihydrochloride, 2,2'-Azobis{2-[1-(2-hydroxyethyl)-2-imidazoline-2-il]propane}dihydrochloride, 2,2'-Azobis{2-[1-(2-hydroxyethyl)-2-imidazoline-2-il]propane}dihydrochloride, 2-(4-hydroxyphenylazo)benzoic acid, 4-(4-hydroxy-phenylazo)-benzoic acid, 4,4'-Azobis(4-cyanovaleric acid) have proved to be of particular interest.

The thermolabile molecule is in turn bound covalently to at least one active molecule, in particular a fluorophore molecule or a drug.

Heating above a certain temperature threshold, which occurs around the nanoparticle following irradiation with the magnetic field, produces homolytic cleavage reactions in the thermolabile molecule with consequent release of the fluorophore or the drug.

In one embodiment of the present invention, several thermolabile molecules are bound to the surface of the nanoparticle so as to allow conjugation with several active molecules, identical to or different from one another, simultaneously.

The active molecules can be selected from the group consisting of drugs and fluorophores.

Preferably the drugs are selected from the group consisting of doxorubicin and indomethacin.

The fluorophore is preferably fluoresceinamine.

In a further embodiment, the covalent bond between the nanoparticle and the thermolabile molecule is obtained by the use of a spacer, preferably a spacer with a radius of gyration between 0.3 and 3 nm, more preferably polyethylene glycol. In the present text the term "radius of gyration" is used to define the dimensions of a polymer chain. It can be determined experimentally by means of scattering techniques (static light scattering, small angle neutron scattering, X-ray scattering). In particular for the purposes of the present invention it is defined by the equation:

$$R_G = 1 \cdot \sqrt{\frac{M_w}{6 \cdot M_{monomer}}}$$

where l is the length of a monomer unit, $M_w$ is the molecular weight of the polymer and $M_{monomer}$ is the molecular weight of the monomer.

In one embodiment, the polyethylene glycol has a molecular weight which varies between 200 Da and 20000 Da, preferably it is 500, 1500 and 8000 Da.

A further embodiment of the invention furthermore provides the use of the system according to the invention for use as a molecular thermometer with a spatial resolution of less than 0.5 nm.

In the present text, "molecular thermometer" means a system able to detect the absolute temperature in very restricted environments, i.e. in the order of a few nanometers.

The thermolabile system of the invention has the following advantages with respect to the known systems: i) it works in solutions at very diluted concentrations (5 nM), in which interparticle interactions are minimised and isothermal conditions are guaranteed; ii) it is able to measure the temperature at different distances from the surface of the nanoparticle, therefore allowing mapping of the temperature gradient thanks to the bond of the fluorophore-thermolabile molecule group with the nanoparticle via macromolecular spacers (for example PEG) of different lengths; iii) it is able to measure the differences between the temperature of the medium of the system and the local temperature around the nanoparticle for long time intervals, since a state of equilibrium is maintained.

Said measurements are all taken with a spatial resolution of less than 0.5 nm.

According to a third embodiment of the invention, use of the system of the invention for the controlled release of at least one drug is provided.

Advantageously, the use of the system of the invention for the controlled release of a drug allows reduction of the mass ratio between the carrier (nanoparticle-spacer-thermosensitive molecule system) of the drug and the drug itself with respect to the known release systems, allows the transport of both hydrophilic and lipophilic drugs, allows control of release of the drug according to the presence and length of the spacer group and the position of the azo group and, lastly, allows transport and release of different drugs from the same nanoparticle: positioning at different distances from the nanoparticle surface furthermore allows the independent release of each of them.

According to a fourth embodiment of the invention, use of the system of the invention for the treatment of a tumour is provided.

Further characteristics of the present invention will become clear from the following description of some merely illustrative and non-limiting examples.

Example 1

Synthesis of the System According to the Invention
Materials and Methods

The 2,2'Azobis-[N-(2-carboxyethyl)-2-methylpropionamide]hydrate (VA057) was purchased from WAKO Chemicals. All the other reagents and compounds were purchased from Sigma-Aldrich. The $^1$H NMR spectra were recorded on a Bruker DRX 400 spectrometer. For determination of the iron concentration, inductively coupled plasma atomic emission spectroscopy (ICP/AES, ThermoFisher, CAP 6000) was used. The samples for the ICP/AES were prepared by incubating 25 µl of sample for one night in 2 ml of aqua regia and subsequently adding Milli-Q water to reach 25 ml. The TEM images were obtained with a JEOL 1011 microscope used at an acceleration voltage of 100 kV. The TEM samples were prepared by drop casting of the solution on a carbon-coated copper grid, leaving the solvent to evaporate. For purification of the iron oxide particles from the free reagents after the synthesis, Amicon centrifuge filters (15 ml, molecular cut-off 100 kDa, Millipore) were used in a centrifuge at controlled temperature (Sigma, 3-16PK). For the ultrapure samples, the free fluorophore or the doxorubicin were removed by double filtering on gel on PD10 desalinization columns (GE Healthcare) with ice cold Milli-Q water as eluant.

The incubation experiments were conducted in a water bath at controlled temperature (Memmert). The alternating magnetic field was applied to the samples in a magneTherm® device (Nanotherics Corp.). Separation of the fluorophore released from the particles was obtained with filtering by, centrifugation in Amicon test tubes (0.5 ml, molecular cut-off 100 kDa, Millipore) in a centrifuge at a fixed angle and controlled temperature (Hettich, Mikro 200R). The fluorescence spectra were recorded with a Cary Eclipse (Varian) spectrometer in microcuvettes with three quartz windows (Hellma).

Synthesis of the Iron Oxide Particles (IONP)

Monodispersed IONP with a core diameter of 15 nm were synthesised as described in Yu et al.[28]. The procedure is shown schematically in FIG. 1.

Briefly, 180 mg (2 mmol) of $Fe_2O_3$ hydrate (catalyst grade, 30-50 mesh), 2.82 g (10 mmol) of oleic acid (technical grade) and 5 g of octadecene were mixed in a three-necked 50 ml flask equipped with a chiller and an inlet for the nitrogen/vacuum. The mixture was degassed under a high vacuum and magnetic excitation for 1 hour. Subsequently, it was heated in a nitrogen atmosphere at 320° C. for 1 hour. After cooling at ambient temperature, the nanoparticles were precipitated twice with isopropanol (5:1 V/V) and a further time with acetone (5:1 V/V) by centrifugation at 3000 rpm/5 min. The iron concentration was determined by ICP-AES and the diameter by TEM as described above (materials and methods).

Synthesis of IONP Derivatized with PEG (IONP-PEG-OH)

Solutions of 500 µmol (85 mg) of gallic acid (GA) dissolved in 50 ml THF and 50 µmol (6 mg) of 4-Dimethylaminopyridine (DMAP) dissolved in 10 ml THF were added under magnetic excitation to a solution of 500 µmol of polyethylene glycol (PEG) (molecular weight ($M_w$)=500, 1500, 8000 Da) dissolved in 100 ml of anhydrous tetrahydrofuran (THF) in a three-necked flask.

The flask was equipped with an inlet for the nitrogen/vacuum and a dropping funnel containing a solution of 2.5 mmol (520 mg) N,N'-Dicyclohexylcarbodiimide (DCC) which was added dropwise over one hour to the PEG/GA/DMAP solution. After mixing for 16 hours in a nitrogen atmosphere, the THF was removed at reduced pressure, obtaining the yellowish raw gallol-PEG (GA-PEG) as a waxy solid. The GA-PEG was dissolved in 100 ml of Milli-Q water at 40° C. in 1 hour, adjusting the acidity to a pH value of 2 by addition of 0.1 M HCl. Said procedure allows crystallization of the hydrolyzed DCC which can be removed by filtration with a paper filter.

In a separator funnel, the GA-PEG was extracted three times from the aqueous phase with chloroform. The solvent was removed from the organic phase at reduced pressure at 60° C. obtaining the GA-PEG in the form of a yellow waxy solid. $^1$H NMR (400 MHz, CDCl$_2$): δ (ppm)=6.98 (Ar—H), 4.64 (CH$_2$-ester), 3.62-3.28 (CH$_2$-PEG, OH-PEG).

The IONP particles encapsulated in oleic acid in chloroform (1 equivalent volume, $c_{Fe}$=10 g/l) were mixed with the solution in chloroform of GA-PEG (1 equivalent volume, 0.1 M in CHCl$_3$) in a separator funnel. Triethyl amine (0.05 equivalent volumes) was added and the mixture was diluted with approximately 5 eq. volumes of toluene. Milli-Q water (5 equivalent volumes) was added and the two phases were emulsified by light stirring. At this point the oleic acid exchange takes place and the IONP tend to segregate at the water-toluene interface. Acetone (approx. 10 eq. volumes) was added to destabilize the particles in the organic phase (toluene/chloroform) and transfer them quantitatively to the aqueous phase. The mixture was lightly stirred again to allow emulsification. After separation of the phases, the aqueous phase was collected.

This step was repeated three times. The residual organic solvents (acetone, toluene) were gradually removed from the aqueous phases at reduced pressure (300 mbar/40° C./30 min, 200 mbar/40° C./30 min, 77 mbar/40° C./30 min).

For purification, the aqueous solution containing the IONP-PEG-OH was diluted in Milli-Q water and reconcentrated on centrifuge filters (molecular cut-off 100 kDa, 3000 rpm). This step was repeated at least five times. Lastly, the iron concentration was determined by ICP-AES.

Synthesis of IONP-PEG-azo-COOH

A solution of 2,2'-Azobis[N-(2-carboxyethyl)-2-methyl propionamide]hydrate (VA057) dissolved in 10 ml of ice cold Milli-Q water was added to a colloidal solution in ice cold water of IONP-PEG-OH (2 ml, $c_{Fe}$=10 g/l). The solution obtained was stirred at 6° C.

10 ml of an ice cold aqueous solution prepared on the spot, containing 10 mg of 1-Ethyl-3-(3-dimethylaminopropyl)carbodiimide (EDC) and 3 mg of DMAP were added to the VA057 solution and the mixture was stirred for 16 hours at 6° C. For purification of the IONP-PEG-azo-COOH thus obtained, the solution was diluted with ice cold Milli-Q water and reconcentrated 5 times on centrifuge filters (molecular cut-off 100 kDa, 3000 rpm) in a centrifuge at controlled temperature at 6° C. The samples were kept at 6° C. and the iron concentration was determined by ICP-AES.

Synthesis of IONP-PEG-azo-FA or IONP-PEG-azo-DOX

The fluoresceinamine (FA, isomer I, 5 mg) or the doxorubicin (DOX, 2.5 mg) were dissolved in 10 ml of THF and were added to an aqueous solution containing IONP-PEG-azo-COOH (2 ml, $c_{Fe}$=10 g/l), 25 mg EDC and 25 mg of N-hydroxysuccinimide (NHS).

The mixture was stirred for 20 minutes at ambient temperature and then cooled rapidly, placing the vial in an ice bath. The THF was removed by nitrogen flow and the end product IONP-PEG-azo-FA(DOX) was purified at least five times by dilution with ice cold Milli-Q water and reconcentrated on centrifuge filters (15 ml, molecular cut-off 100 kDa, 3000 rpm) in a centrifuge at 6° C. To remove the last traces of non-bound FA/DOX, the concentrated samples were passed twice through a filtering column on gel G25 Sephadex at 6° C. The samples were kept at 6° C. and the iron concentrations were determined by ICP-AES.

Example 2

System of the Invention as a Molecular Thermometer

In the approach used by the inventors, the fluoresceinamine (FA) bound covalently to, the 2,2'-Azobis[N-(2-carboxyethyl)-2-methyl propionamide]hydrate (VA057) is bound covalently to the surface of a superparamagnetic monodispersed nanoparticle of iron oxide (IONP) with diameter of 15 nm via polyethylene glycol (PEG) spacers with different molecular weights (IONP-PEG-VA057-FA).

The release of the fluorophore following application of a magnetic field of 9-17 mT modulated at a frequency of 334.5 kHz was then monitored via photoluminescence. The detachment of the fluoresceinamine allows reading of the absolute temperature while the PEG chains act as spacers, allowing sub-nanometric resolution of the temperature measurement.

The quantity of fluoresceinamine molecules released by the system, at pre-set time intervals, is directly correlated to the degree of decomposition of the azo group which in turn depends on the local temperature ($T_{local}$) on the surface of the nanoparticle (for the VA057 the half-life temperature at 10 hours is 57° C. in water). Following application of the magnetic field, the effective local heating can be expressed as the difference LT between the local temperature $T_{local}$ and the global temperature $T_{global}$ (temperature of the medium surrounding the nanoparticles at a great distance from their surface which can be measured with a temperature probe immersed in the solution).

$$\Delta T = T_{local} - T_{global} \quad (1)$$

To obtain the quantitative correlation between the fluoresceinamine released and the local temperature, the calibration curves at different temperatures and at pre-set time intervals were constructed. For these experiments, three stable 5 nM colloidal solutions were prepared in a sodium borate buffer (pH 9) using IONP-PEG-VA057-FA type particles in which the PEG molecular weight is 500, 1500 and 8000 Da respectively. The solutions after preparation were incubated for one hour at different temperatures, between 20 and 80° C. Incubation in a water bath ensures a uniform temperature throughout the sample, so that in this case the local temperature is equal to the global temperature.

The fluorophore released was promptly separated from the particles in solution by centrifugation on a membrane filter (molecular cut-off=100 kDa) and the photoluminescence (PL) spectra were then recorded.

Incubation Experiments

The colloidal solutions of IONP-PEG-azo-FA (molecular weight (PEG)=500, 1500, or 8000 Da) were diluted in an ice cold sodium borate buffer (pH 9, SBB9) to reach a final concentration of cNP=5 nM. These storage solutions were used for the incubation and the experiments with the alternating magnetic field.

To construct the calibration curves, portions of 0.5 ml were placed in 1.5 ml Eppendorf vials and incubated. For each incubation temperature, 3 individual portions were placed in a water bath at controlled temperature for 1 hour. The solutions were then placed in Amicon centrifuge filters (0.5 ml, molecular cut-off 100 kDa) and centrifuged for 5 minutes at 14000 rpm. In this phase, the fluoresceinamine released was washed by the filter while the IONP were blocked on a cellulose acetate membrane. To collect any fluoresceinamine molecules trapped in the filter, 0.5 ml of ice cold sodium borate buffer were added to the dry filter and centrifuged again for 5 minutes at 14000 rpm.

The eluates were collected and kept in the dark before being analysed by fluorescence spectroscopy.

AMF Experiments

A portion of IONP-PEG-azo-FA (molecular weight(PEG)=500, 1500, or 8000 Da) at $c_{NP}$=5 nM in SSB9 was placed in the centre of a coil in the magneTherm device. An optical temperature probe was immersed in the solution to measure in real time the macroscopic temperature which remained constant during the entire measurement and equal to the ambient temperature. Magnetic fields were applied with intensity B 9, 13 or 17 MT for 1 hour and the solutions were then placed on Amicon centrifuge filters (0.5 mL, molecular cut-off 100 kDa) and centrifuged for 5 minutes at 14000 rpm.

The fluoresceinamine released was washed by the filter while the IONP were blocked on a cellulose acetate membrane. To collect any fluoresceinamine molecules trapped in the filter, 0.5 ml of ice cold SSB9 were added to the dry filter and the filter was then centrifuged again for 5 minutes at 14000 rpm.

For each sample with different PEG molecular weight and each magnetic field intensity B the procedure was repeated twice to triplicate the results. The eluates were collected and kept in the dark before being analysed by fluorescence spectroscopy.

Fluorescence Spectroscopy

The eluates of the incubation and the experiments with the magnetic field were analysed by fluorescence spectroscopy. All the samples were recorded the same day to avoid fluctuations in maximum intensity due to the lamps.

The instrument was switched on 1 hour before the measurement to stabilise the temperature of the lamps. The samples were measured in microcuvettes with three quartz windows by excitation at 460 nm (slots 5 nm/5 nm, U(detector)=600 V). The emission signals were collected from 495 to 650 nm.

Results

Figure 2:
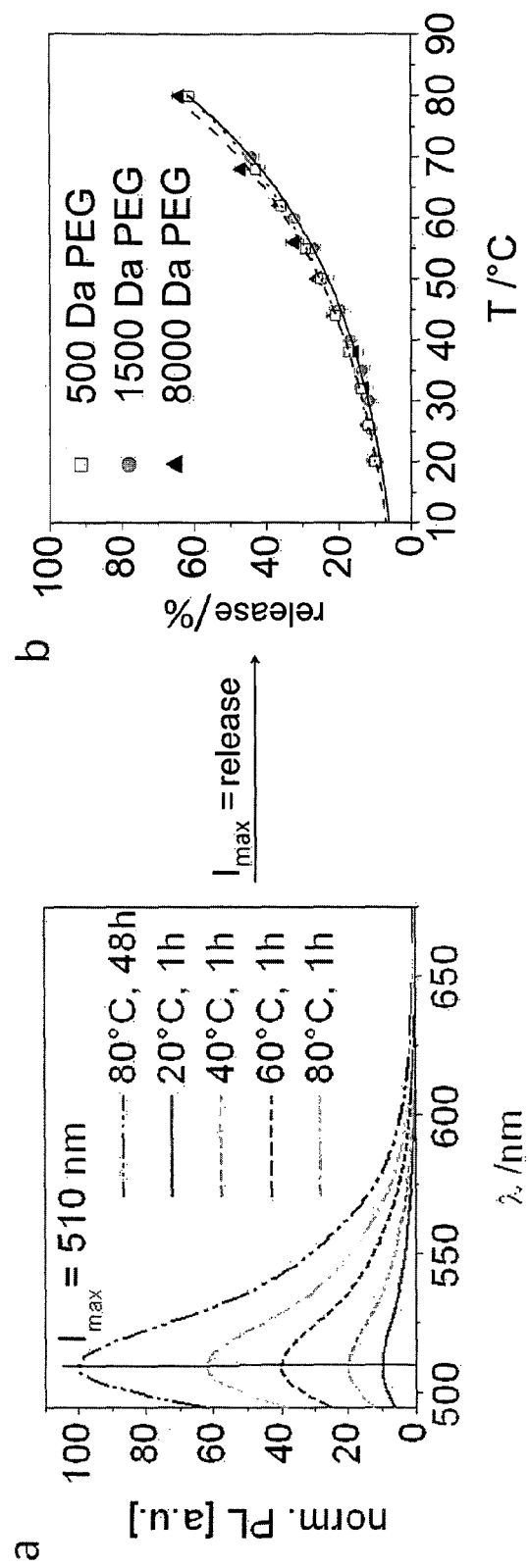
FIG. 2 illustrates the photoluminescence spectra obtained following heating of an IONP-PEG-VA057-FA system at increasing temperatures and with PEG of increasing dimensions according to example 2.

The photoluminescence signal of the samples analysed ($I_{max,incubation}$) increases as the temperature increases (see FIG. 2a). To normalise the maximum photoluminescence to 510 nm, the three samples of the example were incubated at 80° C. for 48 hours and the fluorophore released (100% release) was separated from the nanoparticles in solution by centrifugation. The photoluminescence spectra were then measured and the $I_{max,incubation}$ was normalised on the $I_{max,80° C.,48 h}$. The normalised photoluminescence intensities (calculated as $I_{max}=I_{max,incubation}/I_{max,80° C.,48 h}*100$), which represent the percentage of fluorophore released, are reported as punctiform data in FIG. 2b according to the incubation temperature T. The best fitting of said punctiform data is obtained with an exponential function, the parameters of which are the mean lifetime (t) and the normalised photoluminescence maximum intensity $I_{max,0° C.}$ i.e. when T is equal to 0° C.

The coefficient of determination ($R^2$) was then measured, i.e. the proportion between the variability of the data and the correctness of the statistical model with variation in the molecular weight of the spacer in the three samples. The values of A, t, $R^2$ are reported in table 1.

TABLE 1

Incubation experiments
Fitting parameters for: $I_{max} = A \cdot e^{(T/t)}$

| Sample | A | t | $R^2$ |
|---|---|---|---|
| IONP-500DaPEG-azo-FA | 5.07 | 31.27 | 0.98 |
| IONP-1500DaPEG-azo-FA | 5.56 | 33.27 | 0.99 |
| IONP-8000DaPEG-azo-FA | 5.87 | 33.94 | 0.99 |

The data reported in the table indicate that the decomposition rate of the azo group depends on the molecular weight of the spacer.

With the calibration curves available and measuring the normalised photoluminescence intensity at 510 nm for the samples after exposure to an alternating magnetic field, the local temperature at different distances from the surface of the nanoparticles can be extrapolated with the following formula:

$$T_{local} = \ln\left(\frac{I_{max}}{A} * t\right) \quad (2)$$

The three samples of IONP-PEG-VA057-FA (molecular weight (PEG)=500, 1500, 8000 Da) were then placed in a hyperthermia device (magneTherm® AC system, Nanotherics Corp.).

The temperature of the solution ($T_{global}$) was monitored by means of an optical fibre immersed in the sample solution and the temperature was maintained constant during the entire measurement phase (±1° C. for one hour). The intensity of the magnetic field B was modulated by changing the voltage applied to the coil. A magnetic field varying between 9 and 17 mT modulated at a frequency of 334.5 kHz for 1 hour was then applied and the fluorophore released was separated from the particles by centrifugation on a centrifuge filter (molecular cut-off 100 kDa).

The photoluminescence spectra were then recorded and the $I_{max,AMF}$ were normalised ($I_{AMF}=I_{max,AMF}/I_{max,80° C.,48h}*100$).

By means of the equation (1) and (2) and knowing the $T_{global}$, the difference ΔT between the local temperature and the global temperature was calculated.

The values obtained are reported in table 2.

TABLE 2

| | IONP-PEG-azo-FA | | | | | |
|---|---|---|---|---|---|---|
| Molecular | Photoluminescence for different fields | | | Values of ΔT for different fields | | |
| weight (PEG) [Da] | $PL_{17mT}$ [a.u.] | $PL_{13mT}$ [a.u.] | $PL_{9mT}$ [a.u.] | $ΔT_{17mT}$ [° C.] | $ΔT_{13mT}$ [° C.] | $ΔT_{9mT}$ [° C.] |
| 500 | 41.40 | 29.61 | 27.35 | 43.67 | 33.18 | 30.70 |
| 1500 | 25.63 | 21.36 | 17.88 | 28.85 | 22.78 | 16.87 |
| 8000 | 15.47 | 14.21 | 14.03 | 10.89 | 8.02 | 7.58 |

FIG. 3a shows the values of ΔT according to the magnetic field applied for the three samples with different PEG molecular weight. Significant values of ΔT can be reached up to almost 45° C. if the azo-FA group is bound to the particle by means of very short spacers (500 Da) and the greatest intensity of the magnetic field (17 mT) is used.

Conversely, longer spacers result in LT of approximately 10° C. applying the same intensity.

Two clear tendencies can therefore be identified: ΔT increases linearly with increase in the intensity of the magnetic field B and decreases exponentially with increase in the molecular weight of the spacer. This leads to the conclusion that ΔT is a function of the intensity of the magnetic field B applied (at a given frequency) and of the molecular weight of the spacer (while the latter has a predominant weight of exponential rather than linear correlation between ΔT and the distance).

In a control experiment, to verify the reliability of the results obtained, very small particles (6 nm) of gallol-PEG-azo-FA in which the PEG has a molecular weight of 1500 Da were exposed to different magnetic fields. These particles, known in literature, do not develop an increase in temperature[23].

The gallol-PEG-azo-FA system was prepared as described above. Portions at a concentration of 5 nM were incubated at various temperatures, and the release values of the fluoresceinamine were reported in a dot graph according to the incubation temperature. The best fitting of the punctiform data is obtained with the function $I_{max}=A \cdot e^{(T/t)}$ with A=7.69 and t=27.54 ($R^2$=0.97). From this last formula it is possible to obtain the increase in local temperature after treatment with alternating magnetic field, according to the expression:

$$T_{local} = \ln\left(\frac{I_{max}}{A} * t\right)$$

Figure 4:
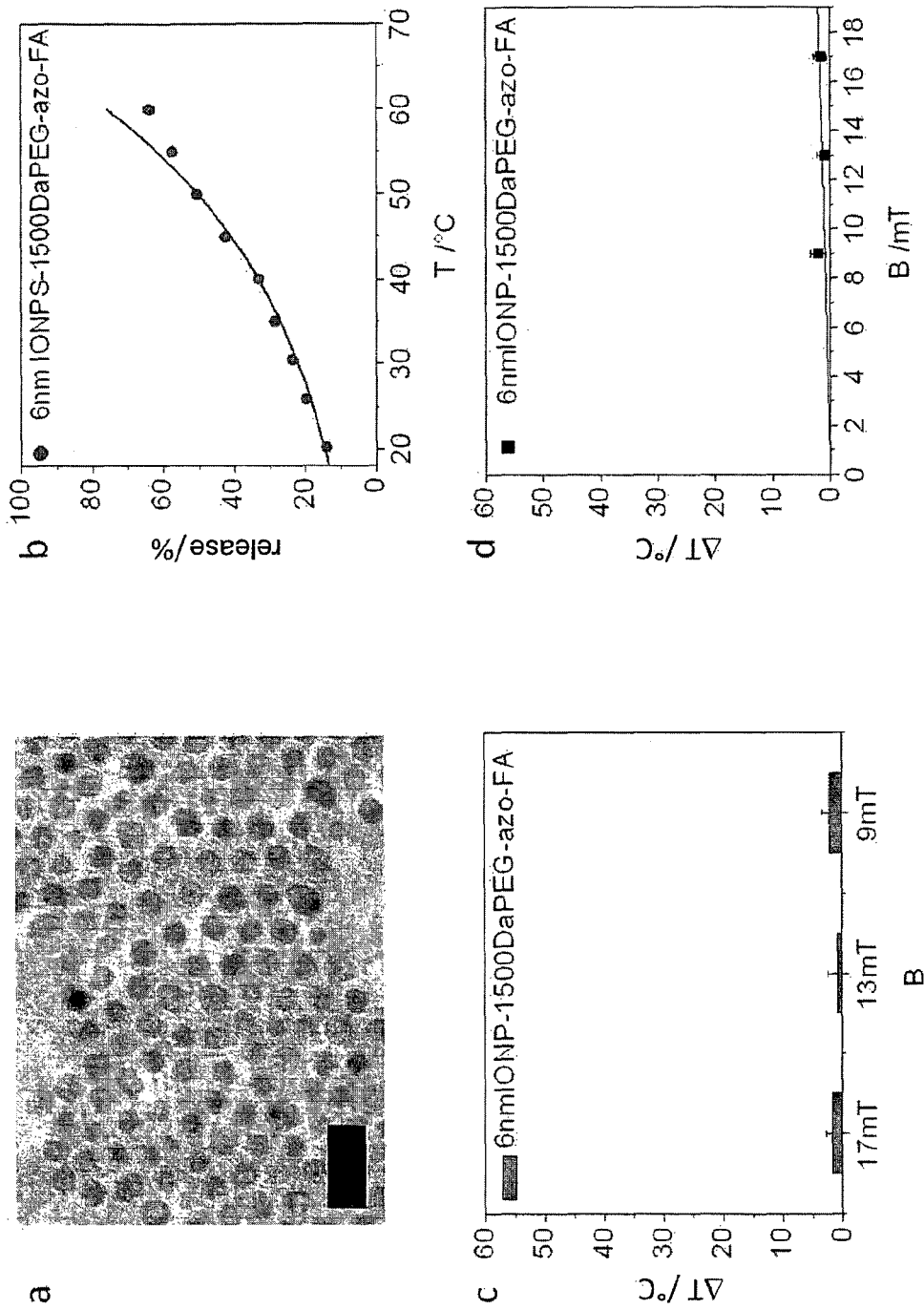
FIG. 4 illustrates a) the TEM image of a gallol-PEG-VA057-FA system with nanoparticles of 6 nm in diameter (the scale is 20 nm); b) the gallol-PEG-VA057-FA calibration curve (6 nm) (after 1 hour of incubation at various temperatures, the fluoresceinamine was separated from the nanoparticles and the photoluminescence intensities of the fluoresceinamine released were recorded. The best fitting of the punctiform data is obtained with the function $I_{max}=A \cdot e^{(T/t)}$ with A=7.69 and t=27.54); c) the values of $\Delta T$ obtained after 1 hour of treatment with the alternating magnetic field; d) the values of $\Delta T$ reported as a function of the intensity of the magnetic field (B)

The results obtained are reported in FIG. 4.

FIGS. 4c and 4d show the values of ΔT for different magnetic field intensities. No local heating is observed for this material.

This experiment clearly shows two points: i) the decomposition of the azo group is due to the variation in local temperature and not to the magnetic field; ii) the intrinsic properties of the paramagnetic particles are crucial for the generation of an appropriate local heating.

FIG. 3b shows the ΔT trend according to B which shows a linear dependence on B for all the PEG spacers. According to the molecular weight, the gradient of the linear trend varies: higher molecular weights result in a lower gradient which can be explained by the different distance of the azo-FA terminal group from the excited surface of the IONP particle. In fact, the nearer the thermolabile group to the source of infinite cooling (the aqueous solution), and therefore the farther it is from the particle surface, the less significant the increase in local temperature as the field increases. Although ΔT would be expected to follow a power law with B as the SAR does for the superparamagnetic nanocrystals, the deviation observed can be attributed to assuming, in the typical measurement of the SAR, the adiabatic conditions that however are far from the conditions used in the experiments conducted for the present invention. In diluted conditions and following excitation over long periods, the system reaches a state of equilibrium in which both global and local temperatures remain constant over time. The medium in which the system of the invention is immersed serves as an infinite cooling source and the flow of heat emitted from the surface of the IONP particles remains constant.

From the experiments conducted it can be concluded that, in isothermal conditions of equilibrium, the temperature increase on the surface of the particles varies linearly with the magnetic field applied.

To obtain the heat gradients dependent on the field, the molecular weight of the spacer can be used to calculate the mean distance of the azo-FA terminal group from the surface. In a polymer arranged at random, the radius of gyration $R_G$ is given by the following expression:

$$R_G = 1 \cdot \sqrt{\frac{M_w}{6 \cdot M_{monomer}}}$$

in which l is the length of a monomer unit, $M_w$ is the molecular weight of the polymer and $M_{monomer}$ is the molecular weight of the monomer. $R_G$ is proportional to the square root of $M_w$, i.e. polymers with a low molecular weight take on a conformation which is more spatially stretched than polymers with a high molecular weight. In the case of the PEG, l is equal to 0.35 nm and $M_{monomer}$ is 44.05 Da and the resulting values of the radius of gyration $R_G$ are reported in table 3 below.

TABLE 3

Radius of gyration of the PEG:

$$R_G = 1 \cdot \sqrt{\frac{M_w}{6 \cdot M_{monomer}}}$$

| $M_w$ [Da] | $M_{monomer}$ [Da] | l [nm] | $R_G$ [nm] |
|---|---|---|---|
| 500 | 44.05 | 0.35 | 0.48 |
| 1500 | 44.05 | 0.35 | 0.83 |
| 8000 | 44.05 | 0.35 | 1.93 |

Figure 3:
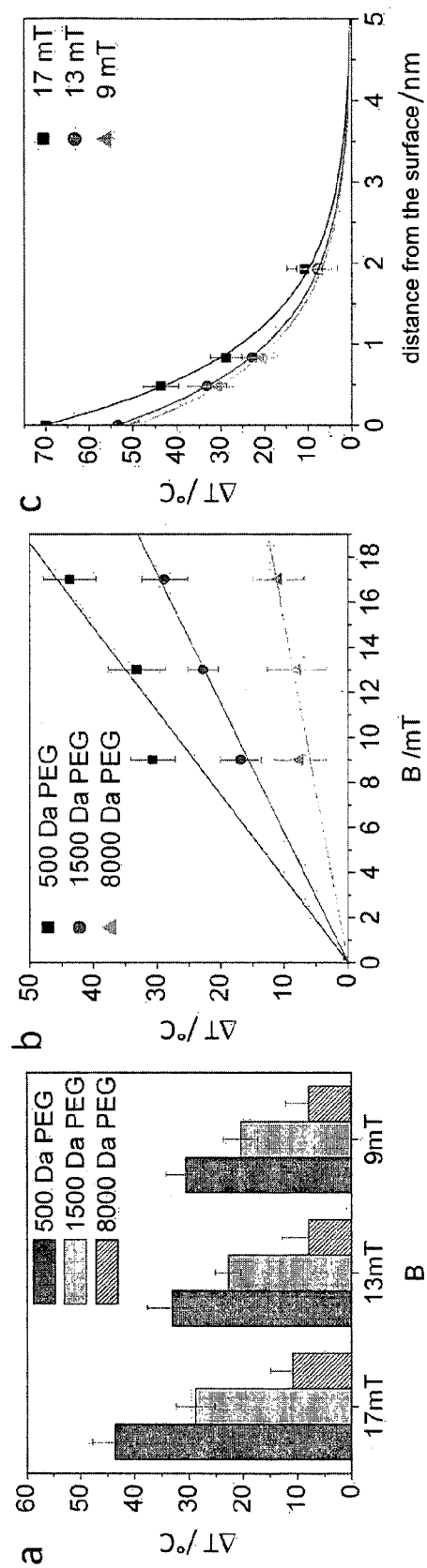
FIG. 3 illustrates the $\Delta T$ values of the experiments conducted in the presence of the alternating magnetic field as illustrated in example 2.

FIG. 3 shows the ΔT trend according to the distance of the azo-FA ($R_G$) group from the surface of the particle. A rapid exponential decrease in ΔT can be observed as the distance from the surface of the particle increases for all the magnetic field intensities applied. For the iron oxide particles, significant temperature variations can be observed for $R_G$ between 0 and 3 nm.

The best fitting of said punctiform data is obtained with an exponential function of the following type:

$$\Delta T = D \cdot e^{-(d/\tau)}$$

in which d (d=RG) is the distance of the azo-FA terminal group from the surface of the particle, D is the temperature on the particle and τ is a measurement of the temperature decay speed according to the distance from the surface of the particle. The fitting parameters are reported in table 4b) below.

TABLE 4

| a) Dependence of ΔT on the field Fitting parameters for $\Delta T = C \cdot B$ | | | | b) Dependence of ΔT on the distance Fitting parameters for $\Delta T = D \cdot e^{-\left(\frac{d}{\tau}\right)}$ | | | |
|---|---|---|---|---|---|---|---|
| $M_w$ [Da] | C [° C./mT] | $R^2$ | B [mT] | D [° C.] | τ [nm] | $R^2$ | |
| 500 | 2.69 | 0.98 | 9 | 49.33 | 0.99 | 0.99 | |
| 1500 | 1.74 | 1.00 | 13 | 53.47 | 1.00 | 1.00 | |
| 8000 | 0.66 | 0.98 | 17 | 70.00 | 0.99 | 0.99 | | where C is the speed of change of ΔT with the field B. The difference between the local temperature at the surface and the global temperature (i.e. for d=0 nm) can be obtained by limiting of the fitting function for d 0 which results in ΔT=D. On the surface, the absolute temperature is given by:

$$T_{abs} = \Delta T_{d=0} + T_{global,mean}$$

The absolute temperature values are reported in table 5 ($\Delta T_{d=0}$ is equal to D in FIG. 3c).

TABLE 5

Calculation of the absolute temperature
$T_{abs} = \Delta T_{d=0} + T_{global,\ mean}$

| Field [mT] | $T_{global,\ mean}$ [° C.] | $\Delta T$ [° C.] | $T_{abs}$ [° C.] |
|---|---|---|---|
| 9 | 22 | 49.33 | 71.33 |
| 13 | 22 | 53.47 | 75.47 |
| 17 | 22 | 70.00 | 92.00 |

For the greater field value tested (17 mT), the absolute temperatures are in the region of the boiling temperature of water. Furthermore these data show that, following the application of an alternating magnetic field and in diluted conditions, the heat generated at the surface of the IONP particles is fairly significant, but limited to the immediate vicinity of the surface of the nanoparticles. The rapid decay profile also confirms the results recently reported in literature, for which the ionic channels of the neurons or of the plasmatic glucose can be adjusted in remote mode by exposure of magnetic nanoparticles to an alternating magnetic field[26,27].

Analogously to the studies now conducted, also in the experiments reported in literature the macroscopic temperature was maintained well below the temperature of activation of the biological effects, therefore suggesting that the biological effects observed were due to temperatures reached only locally by the cell membrane.

The inventors have also found that the effects of local heating are not significantly influenced by the concentration of the nanoparticles, in a certain concentration range. The inventors have found that the same release percentages are obtained, and therefore the same $\Delta T$ values, with nanoparticle concentrations 10 times higher than those used in the experiments reported above. At concentrations below 2 nM the detection limit of the fluorophore FA is reached.

Example 3

Determination of the Doxorubicin Concentration

Figure 5:
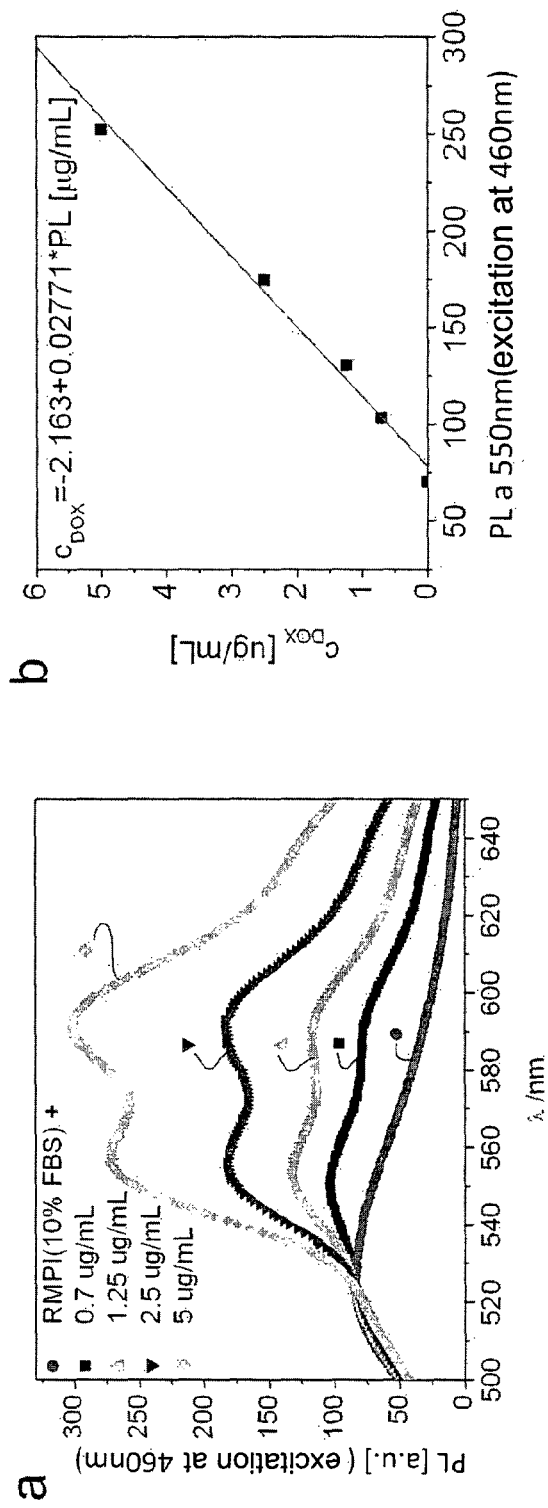
FIG. 5 illustrates a) the spectra of the culture medium RPMI with 10% FBS (white) and of the same medium containing different quantities of doxorubicin; b) the photoluminescence intensities at 550 nm represented as a function of the doxorubicin concentration (the doxorubicin concentration [µg/ml] was obtained by linear interpolation of the punctiform data)

The IONP-PEG-azo-DOX samples prepared in example 1 (molecular weight(PEG)=500, 8000 Da) dispersed in a cell culture medium (RPMI with 10% FBS), were incubated for 48 hours at 80° C. and then centrifuged at 14000 rpm for 10 min to precipitate the IONP, thus separating them from the DOX released (100%) in solution. The supernatants were collected and analysed by fluorescence spectroscopy. The concentration was calculated with the calibration function obtained by measuring the photoluminescence intensity at 550 nm (excitation at 460 nm) of a series of DOX dilutions as reported in FIG. 5.

Dividing the DOX concentration by the concentration of the particles, the number of DOX molecules can be calculated for each particle, i.e. 319 DOX/IONP for the IONP with PEG spacers measuring 500 Da, and 135 DOX/IONP for the IONP with PEG spacers measuring 8000 Da.

Cell Experiments

For the cell viability experiments, both the samples of IONP-PEG-azo-DOX (500 and 8000 Da) were adjusted to a maximum final DOX concentration of 5.5 μg/ml ($C_{NP\text{-}500PEG\text{-}azo\text{-}DOX}$=0.42 μM and $C_{NP\text{-}8000PEG\text{-}azo\text{-}DOX}$=0.92 μM) with a cell culture medium at 6° C. (RPMI with 10% FBS). The dispersions of IONP-PEG-azo-DOX (Mw(PEG)=500 or 8000 Da) in the cell culture medium were centrifuged for 10 minutes at 14000 rpm immediately after the preparation ($T_0$), after 1 hour at ambient temperature ($T_{RT}$) and after 1 hour of treatment with the alternating magnetic field of 17 mT, modulated at a frequency of 334.5 ($T_{AMF}$).

The viability assay was performed using the cell viability reagent PrestoBlue™ (Invitrogen). Briefly, $2 \cdot 10^4$ KB cells were suspended in 0.2 ml of medium added to serum in a plate with 96 wells and left to grow for 24 hours at 37° C. and 5% $CO_2$.

The supernatants obtained from centrifugation of the IONP-PEG-azo-DOX samples (containing different quantities of DOX released by the nanoparticles) were used to treat the cells for 6, 12 and 24 hours. The medium was then removed, the cells were washed with PBS and fresh medium was added.

The fluorescence signals were analysed at 590 nm by means of the TECAN plate reader before (as a blank) and after addition of the cell viability reagent PrestoBlue™ for 30 minutes. Each assay was repeated 3 times and the cytotoxicity values of the supernatants after treatment with the magnetic field ($T_{AMF}$) were compared with the cytotoxicity values of the controls at $T_0$ and $T_{RT}$.

Results

The inventors investigated the release of doxorubicin (DOX) by means of the system of the invention. By positioning the thermolabile group at different distances from the surface of the IONP, so that they correspond to different $\Delta T$ values when the magnetic field is applied, it is possible to control release of the doxorubicin.

For this purpose IONP-PEG-azo-DOX systems were synthesised using PEG spacers with molecular weights equal to 500 and 8000 Da as illustrated in example 1.

The two samples with PEG with different molecular weights were dispersed in a cold (6° C.) cell culture medium and each of them were then divided into three portions. The first portion of each sample was centrifuged directly after the preparation to precipitate the IONP and the supernatant was collected and used as a blank ($T_0$, no release of doxorubicin is expected).

A second portion of each sample was incubated at ambient temperature ($T_{RT}$) for one hour and never exposed to a magnetic field before centrifugation and collection of the supernatant. These samples were used as a control for the release of doxorubicin following thermal decomposition of the azo group at ambient temperature (the temperature of the medium was maintained at $T_{RT}$ throughout the experiment).

For both the samples with PEG with different molecular weights, approximately 12% of doxorubicin is released at ambient temperature following thermal decomposition of the azo group.

A third portion of each sample was treated with a magnetic field of 17 mT, modulated at a frequency of 334.5 kHz for 1 h ($T_{AMF}$)

The quantity of doxorubicin released by means of hyperthermia depends on the local temperature on the surface of the IONP during treatment with the magnetic field. For the system with the PEG with smaller dimensions (500 Da), approximately 36% of doxorubicin was released, while for the system with the PEG with larger dimensions (8000 Da) a release of 15% was observed.

These results correspond to what was observed in the previous example with the fluorophore and lead to the conclusion that neither the suspension medium nor the IONP concentration or the different complex molecule (doxorubicin instead of a fluorophore) influence the decomposition rate of the azo group.

Figure 6:
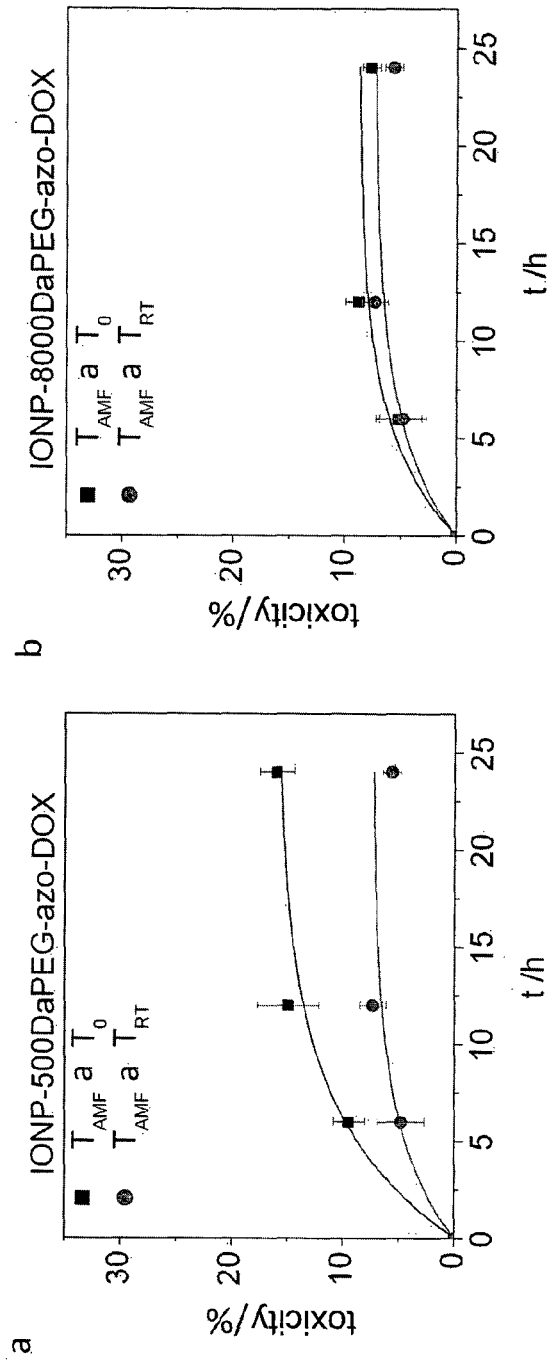
FIG. 6 illustrates the results of the toxicity tests of example 3.

For the cell toxicity experiments, the supernatants collected above ($T_0$, $T_{RT}$, $T_{AMF}$ containing different quantities of doxorubicin after release from the system) were used to treat KB cells for 6, 12 and 24 hours, then measuring the cytotoxic effects with a viability assay (Reagent Presto-Blue™, Invitrogen). The fluorescence signal at 590 nm measured before (as a blank) and after addition of the PrestoBlue reagent permitted reading of the number of live cells in each sample. After treatment with the magnetic field, the system with the PEG 500 released large quantities of doxorubicin compared to the samples at $T_0$ and $T_{RT}$ (see the results in FIG. 6), while the system with the PEG 8000 did not do so. Therefore the cytotoxicity of the sample with the shorter spacer was 3 times greater than that of the sample with the longer spacer. This clearly demonstrates that the release and therefore the thermal decomposition of the azo group strictly depends on the distance of the latter from the IONP particle and therefore on the length of the spacer.

Example 4

Magnetic Characterisation of the Iron Oxide Nano Articles (IONP)

A further proof of the heat generated by the IONP particles with diameter of 15 nm following exposure to an alternating magnetic field was obtained from comparison of the magnetic characterisations of the nanoparticles before and after exposure to the alternating magnetic field or to a thermal treatment. Recording the hysteresis curves, an important improvement was observed in the magnetic properties (i.e. fewer coercive fields and higher saturation magnetisation) for the samples exposed to the magnetic field or to the heat, compared to the samples of nanoparticles that were not heated in local mode. Since macroscopic heating did not occur during application of the magnetic field, it was concluded that the magnetic characteristics measured can only be explained by the local heating of the nanoparticles.

In detail, a first sample of nanoparticles was exposed to a magnetic field of 9-17 mT, modulated at a frequency of 334.5 kHz for six hours. Another portion of the same nanoparticles was subjected to annealing at 140° C. for two hours. In both cases a considerable increase in the magnetic properties was observed (for example lower coercive fields and higher saturation magnetisation). In this regard, the magnetic parameters (see table 6) can also be used as qualitative indicators of the local heating.

Since no macroscopic heating was observed during application of the magnetic field but only an increase in the magnetic properties, these observations support the effect of production of heat by the magnetic nanoparticles when subjected to the magnetic field or to a heating process.

To perform these measurements, the samples were analysed by means of a SQUID Quantum Design MPMSXL magnetometer. For preparation of the sample, a certain volume of sample, (25 µl or 50 µl, from [Fe]=15.6 g/l to [Fe]=6.3 g/l) was isolated and dried or heated by annealing in a Teflon film. After evaporation of the solvent, the powder was removed from the Teflon film and its magnetic properties were measured. The ZFC-FC curves were measured between −268.15° C. and 126.85° C. in a magnetic field of 1989 A/m. The hysteresis cycles were measured up to 7 Tesla and at a temperature of −268.15° C. (see FIGS. 7 and 8); a decrease in the coercive fields is highlighted for the samples during the heating.

Three measurements were taken using the same sample before and after three different treatments.

Figure 7:
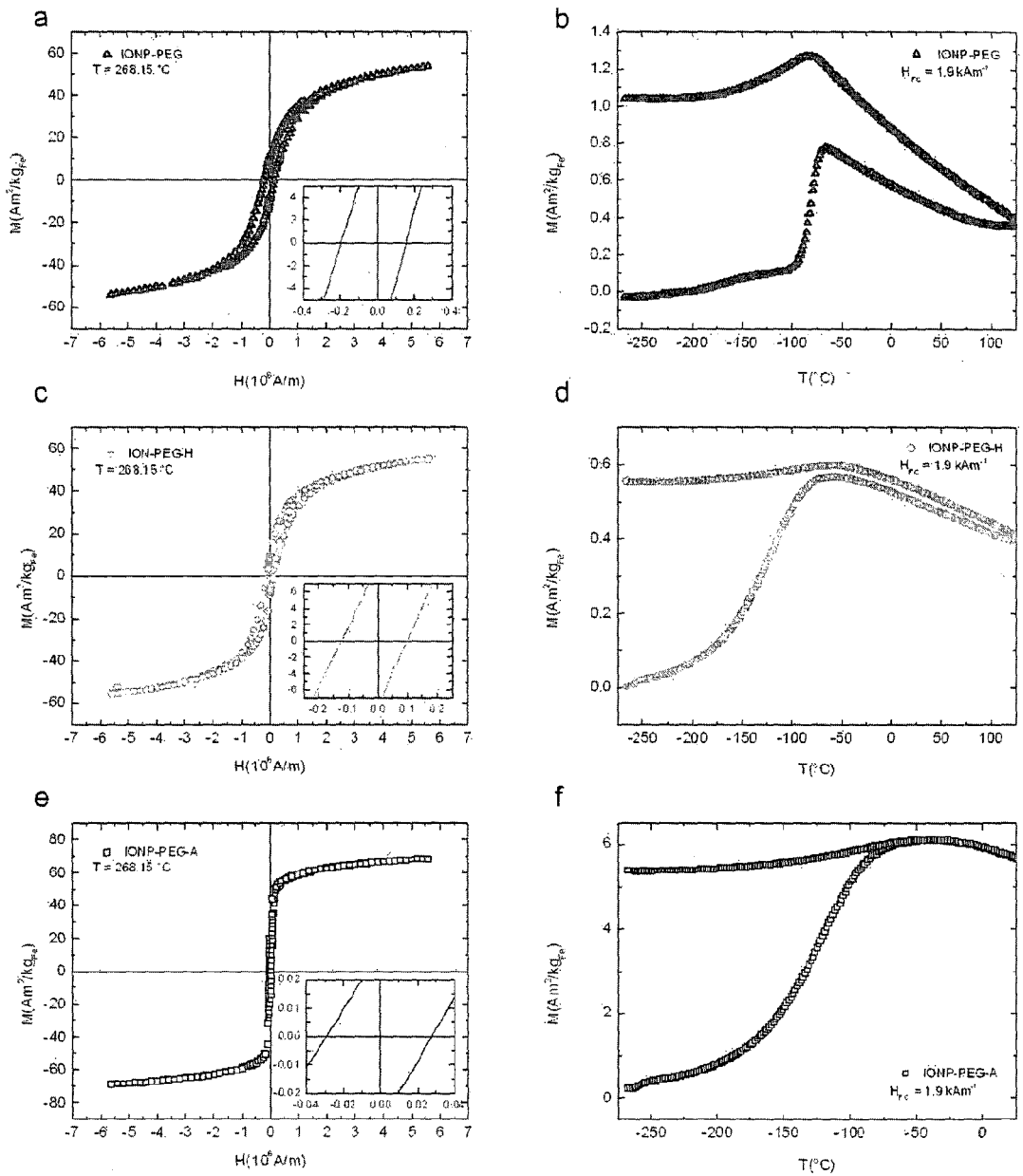
FIG. 7 illustrates the magnetization curves recorded at −268.15° C. (left-hand column) and ZFC-FC measured at 1989 A/m (right-hand column) for iron oxide nanoparticles in different experimental conditions: iron oxide nanoparticles as prepared (IONP-PEG, panels A and B), iron oxide nanoparticles after heating at 140° C. for two hours (IONP-PEG-A, panels E and F) and iron oxide nanoparticles exposed to a magnetic field of 17 mT and frequency of 334.5 kHz for six hours (IONP-PEG-H, panels C and D)
Figure 8:
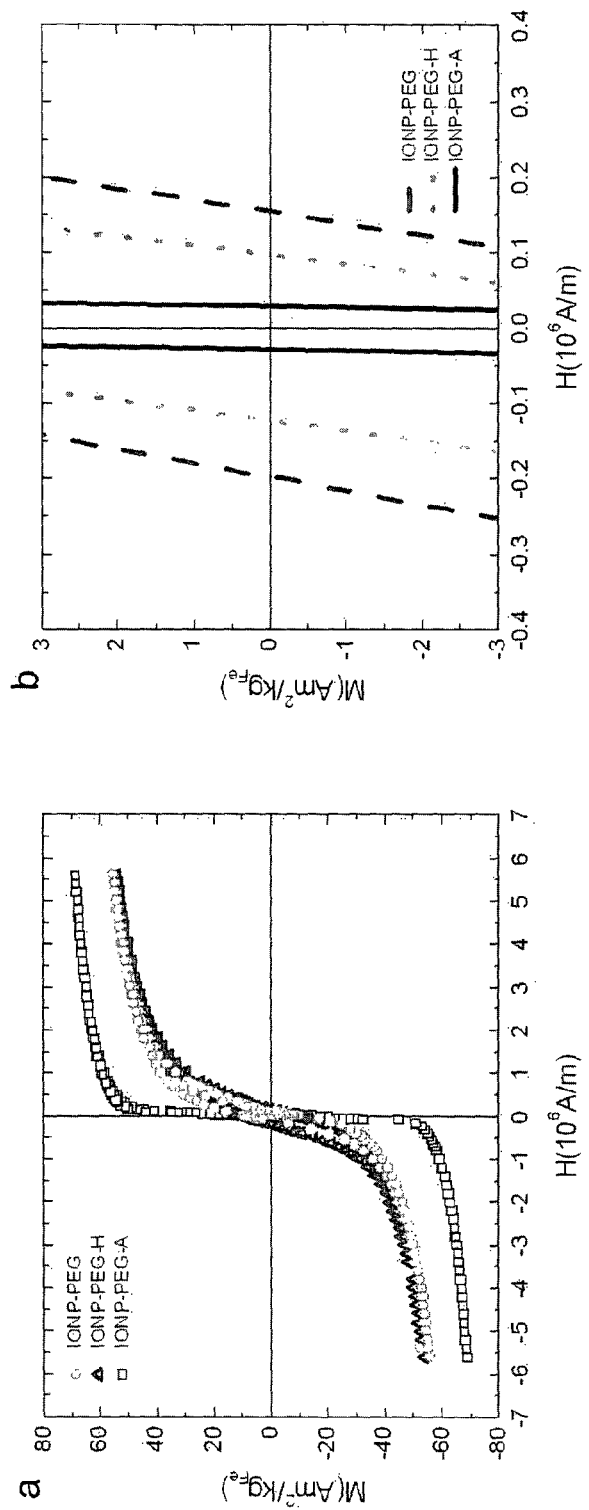
FIG. 8 illustrates the hysteresis cycles for the samples IONP-PEG, IONP-PEG-H and IONP-PEG-A (panel A) and an enlargement of the hysteresis cycles of panel A at low magnetic fields for the samples IONP-PEG (dashed line), IONP-PEG-H (dash-dot line) and IONP-PEG-A (continuous line) of example 4.

For the first measurement, the measurements were performed on iron oxide nanoparticles (sample indicated by the acronym IONP-PEG, shown in FIG. 7, panels A and B). A portion of the same sample was then heated on a plate for two hours to 140° C. (sample indicated by the acronym IONP-PEG-A, shown in FIG. 7, panels E and F). Lastly, the third measurement was taken on a portion of iron oxide nanoparticles after exposure to an alternating magnetic field of 17 mT, modulated at a frequency of 334.5 kHz for 6 hours (sample indicated by the acronym IONP-PEG-H, shown in FIG. 7, panels C and D).

The results obtained are illustrated in table 6 below.

TABLE 6

| Sample | $M_s$ (Am²/kg) | $H_C$ (A/m) | γ (Am²/kg) |
| --- | --- | --- | --- |
| IONP-PEG | 40 | 177060 | $135.32 \cdot 10^{-4}$ |
| IONP-PEG-H | 44 | 109419 | $103.48 \cdot 10^{-4}$ |
| IONP-PEG-A | 61 | 28091 | $81.98 \cdot 10^{-4}$ |

As can be observed, the magnetic properties of the samples change depending on whether the nanoparticles are heated by the heat or by exposure to the magnetic field. These data confirm that the nanoparticles exposed to the magnetic field produce a local heating.

The magnetic characterisation of the derivatized iron oxide nanoparticles (IONP-PEG) identified a boundary temperature of −35.15° C., a saturation magnetisation of 40 Am²/kg, a strong exchange interaction of 21884 A/m together with a broad coercive field of 177060 A/m.

REFERENCES

[1] G. Kong, M. W. Dewhirst, Review Hyperthermia and liposomes. *International Journal of Hyperthermia* 15 (5), 345 (1999).
[2] Kumar, Challa S. S. R. and Mohammad, Faruq, Magnetic nanomaterials for hyperthermia-based therapy and controlled drug delivery. *Advanced Drug Delivery Reviews* 63 (9), 789 (2011).
[3] Guardia, Pablo et al., Water-Soluble Iron Oxide Nanocubes with High Values of Specific Absorption Rate for Cancer Cell Hyperthermia Treatment. *ACS Nano* 6 (4), 3080 (2012).
[4] Lee, Jae-Hyun et al., Exchange-coupled magnetic nanoparticles for efficient heat induction. *Nat Nano* 6 (7), 418 (2011).
[5] Laurent, Sophie, Dutz, Silvio, Häfeli, Urs O., and Mahmoudi, Morteza, Magnetic fluid hyperthermia: Focus on superparamagnetic iron oxide nanoparticles. *Advances in Colloid and Interface Science* 166 (1-2), 8 (2011).
[6] Gazeau, Florence, vy, Michael, and Wilhelm, Claire, Optimizing magnetic nanoparticle design for nanothermotherapy. *Nanomedicine* 3 (6), 831 (2008).
[7] Bae, Ki Hyun et al., Chitosan Oligosaccharide-Stabilized Ferrimagnetic Iron Oxide Nanocubes for Magnetically Modulated Cancer Hyperthermia. *ACS Nano* 6 (6), 5266 (2012).
[8] Ma, Ming et al., Size dependence of specific power absorption of $Fe_3O_4$ particles in AC magnetic field. *Journal of Magnetism and Magnetic Materials* 268 (268), 33 (2004).
[9] Johannsen, M. et al., Clinical hyperthermia of prostate cancer using magnetic nanoparticles: Presentation of a new interstitial technique. *International Journal of Hyperthermia* 21 (7), 637 (2005).
[10] Mornet, S., Vasseur, S., Grasset, F., and Duguet, E., Magnetic nanoparticle design for medical diagnosis and therapy. *J. Mater. Chem.* 14 (14), 2161 (2004).

11 Bothun, Geoffrey D. and Preiss, Matthew R., Bilayer heating in magnetite nanoparticle-liposome dispersions via fluorescence anisotropy. *Journal of Colloid and Interface Science* 357 (1), 70 (2011).

12 Ruiz-Hernández, Eduardo, Baeza, Alejandro, and Vallet-Regí, María, Smart Drug Delivery through DNA/Magnetic Nanoparticle Gates. *ACS Nano* 5 (2), 1259 (2011).

13 Dobson, Jon, Remote control of cellular behaviour with magnetic nanoparticles. *Nat Nano* 3 (3), 139 (2008).

14 Creixell, Mar, Bohórquez, Ana C., Torres-Lugo, Madeline, and Rinaldi, Carlos, EGFR-Targeted Magnetic Nanoparticle Heaters Kill Cancer Cells without a Perceptible Temperature Rise. *ACS Nano* 5 (9), 7124 (2011).

15 Keblinski, P. et al., Limits of localized heating by electromagnetically excited nanoparticles. *Journal of Applied Physics* 100 (5) (2006).

16 Okabe, Kohki et al., Intracellular temperature mapping with a fluorescent polymeric thermometer and fluorescence lifetime imaging microscopy. *Nat Commun* 3, 705 (2012).

17 Yang, Jui-Ming, Yang, Haw, and Lin, Liwei, Quantum Dot Nano Thermometers Reveal Heterogeneous Local Thermogenesis in Living Cells. *ACS Nano* 5 (6), 5067 (2011).

18 Hamad-Schifferli, K. et al., Remote electronic control of DNA hybridization through inductive coupling to an attached metal nanocrystal antenna. *Nature* 415 (6868), 152 (2002).

19 Orfeuil, M, *Electric Process Heating: Technologies/Equipment/Applications*. (Battelle Press, Columbus, Ohio, 1987).

20 Brites, Carlos D. S. et al., A Luminescent Molecular Thermometer for Long-Term Absolute Temperature Measurements at the Nanoscale. *Advanced Materials* 22 (40), 4499 (2010).

21 Vetrone, Fiorenzo et al., Temperature Sensing Using Fluorescent Nanothermometers. *ACS Nano* 4 (6), 3254 (2010).

22 Fischer, Lorenz H., Harms, Gregory S., and Wolfbeis, Otto S., Upconverting Nanoparticles for Nanoscale Thermometry. *Angewandte Chemie International Edition* 50 (20), 4546 (2011).

23 Gupta, A., Kane, R. S., and Borca-Tasciuc, D. A., Local temperature measurement in the vicinity of electromagnetically heated magnetite and gold nanoparticles. *Journal of Applied Physics* 108 (6) (2010).

24 Rosensweig, R. E., Heating magnetic fluid with alternating magnetic field. *Journal of Magnetism and Magnetic Materials* 252 (1-3 SPEC. ISS.), 370 (2002).

25 Riedinger, Andreas et al., Ratiometric Optical Sensing of Chloride Ions with Organic Fluorophore-Gold Nanoparticle Hybrids: A Systematic Study of Design Parameters and Surface Charge Effects. *Small* 6 (22), 2590 (2010).

26 Huang, Heng et al., Remote control of ion channels and neurons through magnetic-field heating of nanoparticles. *Nat Nano* 5 (8), 602 (2010).

27 Stanley, Sarah A. et al., Radio-Wave Heating of Iron Oxide Nanoparticles Can Regulate Plasma Glucose in Mice. *Science* 336 (6081), 604 (2012).

28 Yu, William W., Falkner, Joshua C., Yavuz, Cafer T., and Colvin, Vicki L., Synthesis of monodisperse iron oxide nanocrystals by thermal decomposition of iron carboxylate salts. *Chemical Communications* (20), 2306 (2004).

29 Liliana, Polo-Corrales and Carlos, Rinaldi, Monitoring iron oxide nanoparticle surface temperature in an alternating magnetic field using thermoresponsive fluorescent polymers. Journal of Applied Physics 111 (7), 07B334.

30 Lee, J., Govorov, A. O., and Kotov, N. A., Nanoparticle Assemblies with Molecular Springs: A Nanoscale Thermometer Angewandte Chemie 117 (45), 7605 (2005).

The invention claimed is:

1. A heat sensitive system comprising at least one nanoparticle able to convert an electromagnetic radiation into thermal energy when said nanoparticle is exposed to an alternating magnetic field, said nanoparticle being bound covalently with at least one thermolabile molecule, said thermolabile molecule being covalently bound with at least one active molecule selected from a fluorophore molecule and a drug, wherein said thermolabile molecule comprises an azo —N=N— functional group, and wherein the thermolabile molecule is selected from the group consisting of (2,2'-Azobis[N-(2-carboxyethyl)-2-methylpropionamide] hydrate), (2,2'-Azobis[2-methyl-N-(2-hydroxyethyl)propionamide), 2,2'-Azobis(2-methylpropionamidine)dihydrochloride, 2,2'-Azobis{2-[1-(2-hydroxyethyl)-2-imidazoline-2-yl]propane}dihydrochloride, 2,2'-Azobis{2-[1-(2-hydroxyethyl)-2-imidazoline-2-yl]propane}dihydrochloride, 2-(4-hydroxyphenylazo)benzoic acid, 4-(4-hydroxy-phenylazo)-benzoic acid, 4,4'-Azobis(4-cyanovaleric acid).

2. The system as claimed in claim 1, wherein said nanoparticle is a paramagnetic nanoparticle at ambient temperature.

3. The system as claimed in claim 1, wherein said nanoparticle is produced in a material selected from iron oxide and a ferrite.

4. The system as claimed in claim 1, wherein said covalent bond between said nanoparticle and said thermolabile molecule is obtained by a spacer.

5. The system as claimed in claim 4, wherein said spacer has a radius of gyration between 0.3 and 3 nm.

6. The system as claimed in claim 4, wherein said spacer is a polyethylene glycol.

7. The system as claimed in claim 6, wherein said polyethylene glycol has a molecular weight selected between 200 and 20000 Da.

8. The system as claimed in claim 7, characterised in that said polyethylene glycol has a molecular weight selected from the group consisting of 500, 1500, and 8000 Da.

9. The system as claimed in claim 1, wherein said fluorophore molecule is fluoresceinamine.

10. The system as claimed in claim 1, characterised in that said drug is selected from the group consisting of doxorubicin and indomethacin.

11. The system as claimed in claim 1 for use as a molecular thermometer with a spatial resolution below 0.5 nm.

12. The system as claimed in claim 1 for the controlled release of at least one drug.

13. The system as claimed in claim 1 for use in the treatment of a tumour.

* * * * *